United States Patent [19]

Baird

[11] Patent Number: 4,643,989

[45] Date of Patent: Feb. 17, 1987

[54] INHIBITION OF ALDOSTERONE SECRETION

[75] Inventor: J. Andrew Baird, San Diego, Calif.

[73] Assignee: The Salk Institute for Biological Studies, San Diego, Calif.

[21] Appl. No.: 642,131

[22] Filed: Aug. 17, 1984

[51] Int. Cl.⁴ .............................................. A61K 37/00
[52] U.S. Cl. ...................................................... 514/12
[58] Field of Search ........................................... 514/12

[56] References Cited

PUBLICATIONS

Atarashi et al., Science, 224, 992–994 (1984).
Chartier et al., Biochem. Bioph. Res. Comm., 122(1), 171–4 (1984).
Seidah et al., Proc. Natl. Acad. Sci., U.S.A., 81, 2640–44 (1984).
Rittel et al., Experientia, 32(2), 246 (1976).
Currie et al., Science, 221, 71–73 (1983).
Kangawa et al., Biochem, Biophy. Res. Comm., 118(1), 131–139 (1984).
Chemical Abstracts, 103 (1985) abst. No. 32467u.
De Lean et al., Endocrinology, 1984, vol. 115, No. 4, pp. 1636, 1637 & 1638.
Gutkowska et al., Proceedings of the Society for Experimental Biology and Medicine, 176, pp. 105–108 (1984).
Abstracts, 7th International Congress of Endocrinology, Jul. 1–7, 1984, Abstracts S.136, 488 & 1453, pp. 150, 504 & 987.

Primary Examiner—Donald B. Moyer
Assistant Examiner—F. T. Moezie
Attorney, Agent, or Firm—Fitch, Even, Tabin & Flannery

[57] ABSTRACT

Atrial peptides useful in practising the invention have the formula:

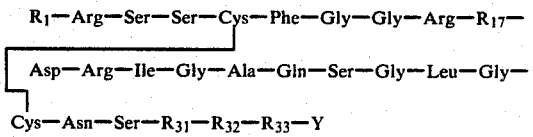

wherein $R_1$ is Arg, Leu-Arg, Ser-Leu-Arg, Arg-Ser-Leu-Arg, Pro-Arg-Ser-Leu-Arg, Gly-Pro-Arg-Ser-Leu-Arg, Ala-Gly-Pro-Arg-Ser-Leu-Arg or Leu-Ala-Gly-Pro-Arg-Ser-Leu-Arg; $R_{17}$ is Met or Ile, $R_{31}$ is Phe or desR$_{31}$; $R_{32}$ is Arg or desR$_{32}$; $R_{33}$ is Tyr or desR$_{33}$; and Y is OH or NH$_2$. These peptides or pharmaceutically acceptable salts thereof, dispersed in a pharmaceutically acceptable liquid or solid carrier, can be administered to mammals, particularly humans, in order to inhibit basal aldosterone secretion and/or to manage aldosterone-dependent hypertention.

18 Claims, No Drawings

INHIBITION OF ALDOSTERONE SECRETION

This invention is directed to use of atrial peptides for treatment of mammals to inhibit secretion of aldosterone and to thereby manage aldosterone-dependent hypertension in mammals.

BACKGROUND OF THE INVENTION

Two atrial peptides obtained from rat atria were characterized by M. G. Currie et al. and are described in the *Science* issue of Jan. 6, 1984. Atriopeptin I has the formula:

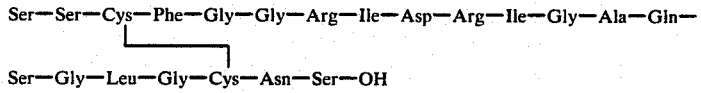

wherein there is a bridging bond between the sulfhydryl groups of the two cysteinyl amino acid residues. Atriopeptin II has the same 21 residues plus the residues Phe and Arg at the C-terminal at positions 22 and 23, respectively.

Atriopeptins I and II are fragments of rANF(1-33), i.e. rat atrial natriuetic factor, as reported in *FEBS Letters*, 167, 2, 352-6, Feb. 1984. rANF and its fragments exhibit potent effects on kidney function and regional vascular resistance; they have natriuretic, diuretic and smooth muscle relaxant activities.

Human ANF(hANF), more specifically hANF-(1-33), is reported in *Biochem. Biophys. Res. Comm.*, 118, 1, 131-9 (1984) and is found to have similar properties.

SUMMARY OF THE INVENTION

Several forms of the polypeptide ANF have recently been isolated and identified from rat and human atria and are presumed to be associated with secretory granules described in atrial tissues. The potent activity of ANF and ANF fragments to increase the sodium content of urine may be mediated by the direct action of these peptides on the kidney. It has now been found that ANF peptides have a high intrinsic activity to directly inhibit basal aldosterone secretion as well as to antagonize the stimulatory effects of adrenocorticotropin (ACTH) and angiotensin II (AN-II) on the secretion of aldosterone by rat adrenoglomerulosa cells. Aldosterone is an adrenocortical steroid which exhibits regulatory influence on metabolism of electrolytes and water. Accordingly, it is believed that ANF and ANF fragments will be of clinical importance in the management of aldosterone-dependent hypertension as a result of the ability of these peptides to modify the adrenocortical response to endogenous ACTH and AN-II.

The atrial peptides which may be employed in the practice of this invention have the following formula:

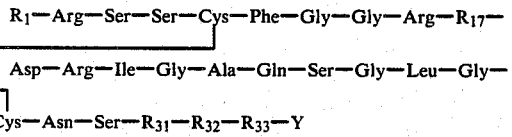

wherein $R_1$ is Arg, Leu-Arg, Ser-Leu-Arg, Arg-Ser-Leu-Arg, Pro-Arg-Ser-Leu-Arg, Gly-Pro-Arg-Ser-Leu-Arg, Ala-Gly-Pro-Arg-Ser-Leu-Arg or Leu-Ala-Gly-Pro-Arg-Ser-Leu-Arg; $R_{17}$ is Met or Ile, $R_{31}$ is Phe or desR$_{31}$; $R_{32}$ is Arg or desR$_{32}$; $R_{33}$ is Tyr or desR$_{33}$; and Y is OH or NH$_2$. These peptides or pharmaceutically acceptable salts thereof, preferably dispersed in a pharmaceutically acceptable liquid or solid carrier, are administered to mammals, particularly humans, in order to inhibit aldosterone secretion and thereby manage aldosterone-dependent hypertension.

DETAILED DESCRIPTION OF THE PREFERRED EMBODIMENTS

The nomenclature used to define these peptides is that specified by Schroder & Lubke, "The Peptides", Academic Press (1965) wherein, in accordance with conventional representation, the amino group appears to the left and the carboxyl group to the right. Where the amino acid residue has isomeric forms, it is the L-form of the amino acid that is represented.

These peptides can be synthesized by a suitable method, such as by exclusively solid-phase techniques, by partial solid-phase techniques, by fragment condensation or by classical solution addition. Alternatively, they may be extracted and purified using the procedures set forth in the aforementioned articles. For example, the techniques of exclusively solid-state synthesis are set forth in the textbook "Solid-Phase Peptide Synthesis", Stewart & Young, Freeman & Co., San Francisco, 1969 and are exemplified by the disclosure of U.S. Pat. No. 4,105,603, issued Aug. 8, 1978 to Vale et al. The fragment condensation method of synthesis is exemplified in U.S. Pat. No. 3,972,859 (Aug. 3, 1976). Other available syntheses are exemplified by U.S. Pat. No. 3,842,067 (Oct. 15, 1974) and U.S. Pat. No. 3,862,925 (Jan. 28, 1975). Synthesis by the use of recombinant DNA techniques may also be used when no unnatural residues are present and should be understood to include the suitable employment of a structural gene coding for the desired form of analog. The synthetic peptide may be obtained by transforming a microorganism using an expression vector including a promoter and operator together with such structural gene and causing such transformed microorganism to express the peptide. A non-human animal may also be used to produce the peptide by genefarming using such a structural gene and the general techniques set forth in U.S. Pat. No. 4,276,282 issued June 30, 1981 or using microinjection of embryos as described in No. WO83/01783 published May 26, 1983 and No. WO82/04443 published Dec. 23, 1982. The synthetic peptide is then suitably recovered from the animal by extraction from sera or the like.

Common to chemical syntheses of the preferred peptides is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues linked to the side-chain protecting groups.

The intermediate of hANF(1-33) has the formula: $X^1$-Leu-Ala-Gly-Pro-Arg($X^4$)-Ser($X^2$)-Leu-Arg($X^4$)-Arg($X^4$)-Ser($X^2$)-Ser($X^2$)-Cys($X^3$)-Phe-Gly-Gly-Arg($X^4$)-Met-Asp($X^5$)-Arg($X^4$)-Ile-Gly-Ala-Gln($X^6$)-Ser($X^2$)-Gly-Leu-Gly-Cys($X^3$)-Asn($X^6$)-Ser($X^2$)-Phe-Arg($X^4$)-Tyr($X^7$)-$X^8$ wherein: the R-groups are as hereinbefore defined; $X^1$ is either hydrogen or an α-amino protecting group. The α-amino protecting groups contemplated by $X^1$ are those known to be useful in the art in the step-wise synthesis of polypeptides. Among the classes of α-amino protecting groups covered by $X^1$ are (1) acyl-type protecting groups, such as formyl, trifluoroacetyl, phthalyl, p-toluenesulfonyl(-Tos), benzensulfonyl, nitrophenylsulfenyl, tritylsulfenyl, o-nitrophenoxyacetyl, chloroacetyl, acetyl, and γ-chlorobutyryl; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as fluorenylmethyloxycarbonyl(FMOC), cyclopentyloxycarbonyl, adamantyloxycarbonyl, and cyclohexyloxycarbonyl; (5) thiourethan-type protecting groups, such as phenylthiocarbonyl; (6) alkyl-type protecting groups, such as triphenylmethyl(trityl), benzyl(Bzl); (7) trialkylsilane groups, such as trimethylsilane. The preferred α-amino protecting group is BOC.

$X^2$ is a protecting group for the hydroxyl group of Ser and is preferably selected from the class consisting of acetyl(Ac), benzoyl(Bz), tert-butyl, trityl, tetrahydropyranyl, benzyl ether(Bzl), 2,6-dichlorobenzyl and Z. The most preferred protecting group is Bzl. $X^2$ can be hydrogen, which means there is no protecting group on the hydroxyl group.

$X^3$ is a protecting group for Cys preferably selected from the class consisting of p-methoxybenzyl(MeOBzl), p-methylbenzyl, thioethyl, acetamidomethyl, trityl and Bzl. The most preferred protecting group is p-methoxybenzyl. $X^3$ can also be hydrogen, meaning that there is no protecting group on the sulfur.

$X^4$ s a protecting group for the guanidino group of Arg preferably selected from the class consisting of nitro, Tos, Z, adamantyloxycarbonyl and BOC, or is hydrogen. Tos is most preferred.

$X^5$ is hydrogen or an ester-forming protecting group for the β-carboxyl group of Asp preferably selected from the class consisting of Bzl, 2,6-dichlorobenzyl(DCB), CBZ, methyl and ethyl. OBzl is most preferred.

$X^6$ is hydrogen or a protecting group for the amido group of Gln or Asn and is preferably xanthyl(Xan).

$X^7$ is a protecting group for the phenolic hydroxyl group of Tyr selected from the group consisting of tetrahydropyranyl, tert-butyl, trityl, benzyl, benzyloxycarbonyl, 4-bromobenzyloxycarbonyl and DCB, the latter being preferred. Alternatively $X^7$ may be hydrogen.

$X^8$ is selected from the class consisting of OH, OCH₃, amides, hydrazides and esters, including an amide, a benzyl ester or a hydroxymethyl ester anchoring bond used in solid phase synthesis for linking to a solid resin support, represented by the formulae:

—NH—benzhydrylamine (BHA) resin support,

—NH—paramethylbenzhydrylamine (MBHA) resin support,

—O—CH₂—polystyrene resin support and

O—CH₂—benzyl-polystyrene resin support

The polystyrene polymer is preferably a copolymer of styrene with about 0.5 to 2% divinyl benzene as a cross-linking agent, which causes the polystyrene polymer to be completely insoluble in certain organic solvents.

In the formula for the intermediate, at least one of $X^1$, $X^2$, $X^3$, $X^4$, $X^5$, $X^6$ and $X^7$ is a protecting group or resin support. In selecting a particular side chain protecting group to be used in the synthesis of the peptides, the following rules are followed: (a) the protecting group should be stable to the reagent and under the reaction conditions selected for removing the α-amino protecting group at each step of the synthesis, (b) the protecting group should retain its protecting properties and not be split off under coupling conditions and (c) the side chain protecting group must be removable, upon the completion of the synthesis containing the desired amino acid sequence, under reaction conditions that will not alter the peptide chain.

The peptides are preferably prepared using solid phase synthesis, such as that described by Merrifield, *J. Am. Chem. Soc.*, 85, p 2149 (1964), although other equivalent chemical syntheses known in the art can also be used as previously mentioned. Solid-phase synthesis is commenced from the C-terminal end of the peptide by coupling a protected α-amino acid to a suitable resin. Such a starting material can be prepared by attaching α-amino- and DCB-protected Tyr to a chloromethylated resin or to a hydroxymethyl resin. The preparation of the hydroxymethyl resin is described by Bodansky et al., *Chem. Ind.* (London) 38, 1597-98 (1966). Chloromethylated resins are commercially available from Bio Rad Laboratories, Richmond, Calif. and from Lab. Systems, Inc. The preparation of such a resin is described by Stewart et al., "Solid Phase Peptide Synthesis" (Freeman & Co., San Francisco 1969), Chapter 1, pp 1-6.

Tyr protected by BOC and by DCB is coupled to the chloromethylated polystyrene resin according to the procedure of Horiki et al. *Chemistry Letters*, pp 165-168, 1978. Following the coupling of BOC-(DCB)Tyr to the resin support, the α-amino protecting group is removed, as by using trifluoroacetic acid(TFA) in methylene chloride, TFA alone or with HCl in dioxane. Preferably 50 weight % TFA in methylene chloride is used with 0-5 weight % 1,2 ethane dithiol. The deprotection is carried out at a temperature between about 0° C. and room temperature. Other standard cleaving reagents and conditions for removal of specific α-amino protecting groups may be used as described in Schroder & Lubke, "The Peptides", 1 pp 72-75 (Academic Press 1965).

After removal of the α-amino protecting group of Tyr, the remaining α-amino- and side chain-protected amino acids are coupled step-wise in the desired order to obtain the intermediate compound defined hereinbefore. As an alternative to adding each amino acid separately in the synthesis, some of them may be coupled to one another prior to addition to the solid phase reactor. The selection of an appropriate coupling reagent is within the skill of the art. Particularly suitable as coupling reagents are N,N'-dicyclohexyl carbodiimide (DCCI) and N,N'-diisopropylcarbodiimide(DICI).

The activating reagents used in the solid phase synthesis of the peptides are well known in the peptide art. Examples of suitable activating reagents are: (1) carbodiimides, such as N,N'-diisopropyl carbodiimide, N-ethyl-N'-(3-dimethylaminopropyl)carbodiimide; (2) cyanamides such as N,N'-dibenzylcyanamide; (3) keteimines; (4) isoxazolium salts, such as N-ethyl-5-phenyl isoxazolium-3'-sulfonate; (5) monocyclic nitrogen-containing heterocyclic amides of aromatic character containing one through four nitrogens in the ring, such as imidazolides, pyrazolides, and 1,2,4-triazolides. Specific heterocyclic amides that are useful include N,N'-carbonyl diimidazole, N,N'-carbonyl-di-1,2,4-triazole; (6) alkoxylated acetylene, such as ethoxyacetylene; (7) reagents which form a mixed anhydride with the carboxyl moiety of the amino acid, such as ethylchloroformate and isobutylchloroformate and (8) nitrogen-containing heterocyclic compounds having a hydroxy group on one ring nitrogen, such as N-hydroxyphthalimide, N-hydroxysuccinimide and 1-hydroxybenzotriazole(HOBT). Other activating reagents and their use in peptide coupling are described by Schroder & Lubke, supra, in Chapter III and by Kapoor, *J. Phar. Sci.*, 59, pp 1–27 (1970).

Each protected amino acid or amino acid sequence is introduced into the solid phase reactor in about a two-to fourfold excess, and the coupling is carried out in a medium of dimethylformamide(DMF):CH$_2$Cl$_2$ (1:1) or in DMF or CH$_2$Cl$_2$ alone. In instances where the coupling is carried out manually, the success of the coupling reaction at each stage of the synthesis is monitored by the ninhydrin reaction, as described by E. Kaiser et al., *Anal. Biochem.* 34, 595 (1970). In cases where incomplete coupling occurs, the coupling procedure is repeated before removal of the α-amino protecting group prior to the coupling of the next amino acid. The coupling reactions can be performed automatically, as on a Beckman 990 automatic synthesizer, using a program such as that reported in Rivier et al., *Biopolymers*, 1978, 17, pp. 1927–1938.

After the desired amino acid sequence has been completed, the intermediate peptide is removed from the resin support by treatment with a reagent, such as liquid hydrogen fluoride, which not only cleaves the peptide from the resin but also cleaves all remaining side chain protecting groups $X^2$, $X^3$, $X^4$, $X^5$, $X^6$ and $X^7$ and the α-amino protecting group $X^1$, to obtain the peptide in its linear form. The cyclic form of the peptide is obtained by oxidizing using a ferricyanide solution, preferably as described Rivier et al., *Biopolymers*, Vol. 17 (1978), 1927–38, or by air oxidation, or in accordance with other known procedures.

As an alternative route, the intermediate peptide may be separated from the resin support by alcoholysis after which the recovered C-terminal ester is converted to the acid by hydrolysis. Any side chain protecting groups may then be cleaved as previously described or by other known procedures, such as catalytic reduction (e.g. Pd on BaSO$_4$). When using hydrogen fluoride for cleaving, anisole and methylethyl sulfide are included in the reaction vessel for scavenging.

The following Example sets forth a suitable method for synthesizing an atrial peptide by the solid-phase technique.

EXAMPLE I

The synthesis of the peptide rANF(8–33) having the formula:

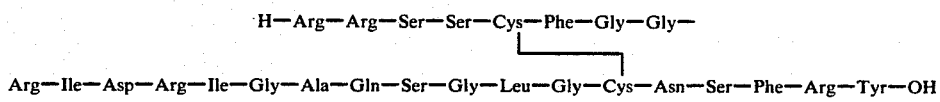

Arg—Ile—Asp—Arg—Ile—Gly—Ala—Gln—Ser—Gly—Leu—Gly—Cys—Asn—Ser—Phe—Arg—Tyr—OH is conducted in a stepwise manner on a chloromethylated resin, such as LS-601 available from Lab Systems, Inc., containing 0.9 Meq Cl/gm. resin. Coupling of BOC-Tyr(DCB) to the washed resin is performed by the procedure set forth by Horiki et al., in *Chemistry Letters* (Chem. Soc. of Japan, 1978) pp. 165–168, and it results in the substitution of about 0.35 mmol. Tyr per gram of resin. All solvents that are used are carefully degassed, preferably by sparging with an inert gas, e.g., helium, to insure the absence of oxygen.

The coupling reaction is carried out in the reaction vessel of a Beckman Model 990 automatic peptide synthesizer which is programmed to perform the following general work cycle: (a) methylene chloride; (b) 60% trifluoroacetic acid in methylene chloride (2 times for 10 and 15 min resp.); (c) isopropyl alcohol wash; (d) 10% triethylamine in methylene chloride (2 times alternated with methanol wash); and (e) methylene chloride wash.

The washed resin (2 g.) is stirred with 1.5 mmoles of BOC-Tyr(DCB) in methylene chloride and diisopropylcarbodiimide (1.5 mmoles) was added. The mixture was stirred at room temperature for 1 hour and the amino acid resin was then washed successively with methylene chloride, ethanol and methylene chloride (3 times each). The protected, attached amino acid was then cycled through steps (b) through (h) in the above wash program. The remaining amino acids (1.5 mmoles) are then coupled successively by the same cycle of events.

After deprotection and neutralization, the peptide chain is built step-by-step on the resin. Generally, one to two mmol. of BOC-protected amino acid in methylene chloride is used per gram of resin, plus one equivalent of 2 molar DCCI or diisopropylcarbodiimide in methylene chloride, for two hours. When BOC-Arg(Tos) or BOC-Asn(Xan) or BOC-Gln(Xan) is being coupled, a mixture of 90% DMF and methylene chloride is used. Bzl is used as the hydroxyl side-chain protecting group for Ser. P-nitrophenyl ester(ONp) can also be used to activate the carboxyl end of Asn, and BOC-Asn(ONp) is coupled overnight using one equivalent of HOBt in a 90% mixture of DMF and methylene chloride. Gln can also be similarly coupled. Alternatively, BOC-Asn and BOC-Gln are coupled using 1 meq. HOBt and 1 meq. DCCI in DMF. Tos is used to protect the guanidino group of Arg, and the aspartic carboxyl group is protected by OBzl. The amido group of Asn is protected by Xan. At the end of the synthesis, the following composition is obtained: BOC-Arg(Tos)-Arg(Tos)-Ser(Bzl)-Ser(Bzl)-Cys(MeOBzl)-Phe-Gly-Gly-Arg(Tos)-Ile-Asp(OBzl)-Arg(Tos)-Ile-D-Ala-Ala-Gln(Xan)-Ser(Bzl)-Gly-Leu-Gly-Cys(MeOBzl)-Asn(Xan)-Ser(Bzl)-Phe-Arg(Tos)-Tyr(DCB)-O-CH$_2$-benzene-polystyrene resin support.

In order to cleave and deprotect the resulting protected peptide-resin, it is treated with 1.5 ml. anisole, and 15 ml. hydrogen fluoride (HF) per gram of peptide-resin, first at $-20°$ C. for 20 min. and then at $0°$ C. for one-half hour. After elimination of the HF under high vacuum, the resin-peptide is washed with dry diethyl ether, and the peptide is then extracted with de-gassed 2N aqueous acetic acid and separated from the resin by filtration.

The cleaved and deprotected peptide is then air-oxidized under high dilution or is added dropwise to a potassium ferricyanide solution to form the disulfide bond between the Cys residues, as described by Rivier et al. in *Biopolymers*, Volume 17 (1978) pp. 1927–1938. After cyclization using the ferricyanide method, the peptide is chromatographed on both anion- and cation-exchange resins using the methods described in the Rivier et al. article and then lyophilized.

The peptide is then purified by gel permeation followed by semi-preparative HPLC as described in Rivier et al., *Peptides: Structure and Biological Function* (1979) pp. 125–128. The chromatographic fractions are carefully monitored by HPLC, and only the fractions showing substantial purity were pooled.

To check whether the precise composition was achieved, the analog is hydrolyzed in sealed evacuated tubes containing 4N methanesulfonic acid and 0.2% tryptamine for 24 hours at $110°$ C. Amino acid analyses of the hydrolysates using a Beckman 121 MB amino acid analyzer shows that the 26-residue peptide structure is obtained.

EXAMPLE II

Rat adrenoglomerulosa cells are obtained by enzymatic digest of adrenals harvested from peripubertal male Sprague Dawley rats(Holtzman, 125 g) using previously described methods, and testing is carried out to determine the effect of synthetic rANF(8–33) on the basal secretion of aldosterone by rat glomerulosa cells. Rat glomerulosa cells are prepared by enzymatic digestion of 20 rat adrenals after ennucleation. The cells remaining on the capsule are digested for 30 minutes with a mixture of collagenase and DNase (4 mg/ml, 4 μg/ml). Dispersed cells are filtered through gauze and centrifuged at 800 rpm for 15 minutes. The pellet is resuspended in M199 buffer containing 0.1% bovine serum albumin(BSA), and the cells are centrifuged at 800 rpm for 15 minutes. The cell pellet is again resuspended in M199-0.1% BSA buffer and distributed in 900-μl aliquots to 12×75 plastic tubes. The samples are preincubated for 90 minutes in a $37°$ C. waterbath under an atmosphere of 5% CO$_2$-95% O$_2$. Aliquots of the test samples are added in a 100 μl volume and incubated for 4 hours. Aldosterone and corticosterone are measured by radioimmunoassay using antisera purchased from Endocrine Sciences, Oxnard, Calif. and [$^3$H]-labelled steroid from New England Nuclear, Boston, Mass. Results are the mean±SEM of 7 replicates. Statistical analysis is performed by analysis of variance, and all points are significant (p<0.01) from control. In concentrations as low as $\leq 10^{-9}$M, there is a significant (p<0.01) inhibition of aldosterone synthesis that is even more accentuated when the higher concentrations are tested (p<0.001).

Similar inhibitory effects on aldosterone formation are obtained when its secretion by the glomerulosa cells in vitro is stimulated with either ACTH or AN-II. Rat glomerulosa cells are prepared as described above and are incubated with synthetic human adrenocorticotropin (ACTH) either alone or in combination with equimolar amounts of ANF(8–33). Aldosterone secretion is measured as above by radioimmunoassay. Other cells are incubated with synthetic angiotensin-11 (AN-II) either alone or in the presence of equimolar amounts of ANF(8–33). Results are the mean±SEM of 7 replicates, and all points are significant when compared to their respective control (p<0.001).

In each of these instances, the simultaneous addition of equimolor amounts of the secretagogues and ANF-(8–33) results in a significant inhibition of aldosterone secretion (p<0.001) when compared to that obtained by the secretagogue alone. In these samples, corticosterone formation is inhibited by $10^{-7}$M ANF(8–33), resulting in decreases from 24.7±0.8 to 7.8±0.3 ng/ml (p 0.001) in basal corticosterone formation, decreases from 37.2±1.4 to 21.9±0.9 ng/ml (p<0.001) in AN-II-stimulated corticosterone formation and decreases from 43.4±0.7 to 36.1±0.7 ng/ml (p<0.001) in ACTH-stimulated corticosterone formation, suggesting that ANF acts early in the steps of steroidogenesis, possibly as early as, or even prior to, cholesterol side-chain cleavage. In other experiments, ANF(8–33) had no effect on pituitary ACTH secretion.

EXAMPLE III

The peptide hANF(8–33), having the formula:
H-Arg-Arg-Ser-Ser-Cys-Phe-Gly-Gly-Arg-Met-Asp-Arg-Ile-Gly-Ala-Gln-Ser-Gly-Leu-Gly-Cys-Asn-Ser-Phe-Tyr-OH is synthesized using the same general procedure as set forth in Example I. Amino acid analysis shows that the desired peptide structure is obtained. Testing as set forth in Example II shows comparable results.

EXAMPLE IV

The peptide hANF(8–33)—NH$_2$, having the formula:

H—Arg—Arg—Ser—Ser—Cys—Phe—Gly—Gly—Arg—Met—Asp—
                        |                                    |
Arg—Ile—Gly—Ala—Gln—Ser—Gly—Leu—Gly—Cys—Asn—Ser—Phe—Tyr—NH$_2$ is synthesized using the same general procedure as set forth in Example I but employing a MBHA resin. Amino acid analysis shows that the desired peptide structure is obtained. Testing as set forth in Example II shows comparable results.

EXAMPLE V

The peptide hANF(5–33), having the formula:

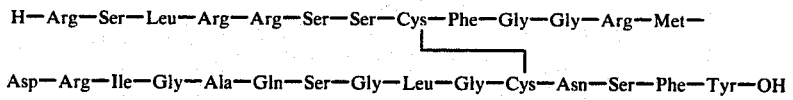

is synthesized using the same general procedure as set forth in Example I. Amino acid analysis shows that the desired peptide structure is obtained. Testing as set forth in Example II shows comparable results.

EXAMPLE VI

The peptide hANF(3-33), having the formula:

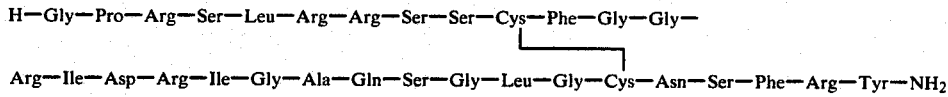

is synthesized using the same general procedure as set forth in Example I. Amino acid analysis shows that the desired peptide structure is obtained. Testing as set forth in Example II shows comparable results.

EXAMPLE VII

The peptide hANF(1-33), having the formula:

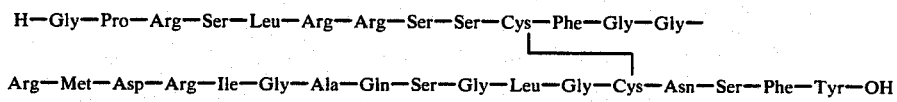

is synthesized using the same general procedure as set forth in Example I. Amino acid analysis shows that the desired peptide structure is obtained. Testing as set forth in Example II shows comparable results.

EXAMPLE VIII

The peptide rANF(5-33), having the formula:

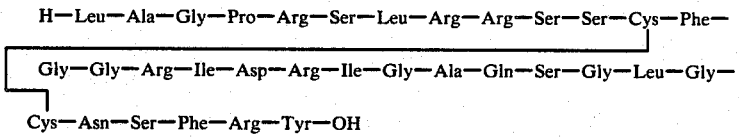

desired peptide structure is obtained. Testing as set forth in Example II shows comparable results.

EXAMPLE IX

The peptide rANF(3-33)—NH$_2$, having the formula:

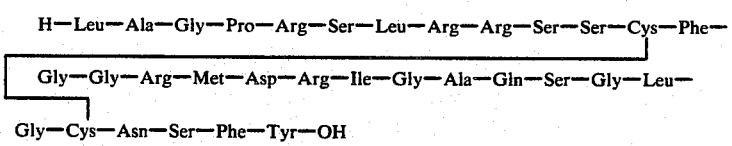

is synthesized as set forth in Example IV. Amino acid analysis shows that the desired peptide structure is obtained. Testing as set forth in Example II shows comparable results.

EXAMPLE X

The peptide rANF(1-33), having the formula:

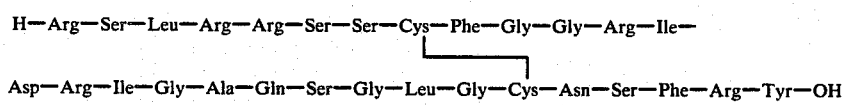

is synthesized using the same general procedure as set forth in Example I. Amino acid analysis shows that the desired peptide structure is obtained. Testing as set forth in Example II shows comparable results.

EXAMPLE XI

The peptide rANF(8-32)—NH$_2$, having the formula:

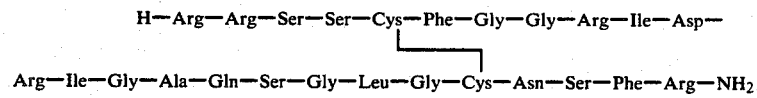

is synthesized as set forth in Example IV. Amino acid analysis shows that the desired peptide structure is ob-

EXAMPLE XII

The peptide rANF(8-30), having the formula:

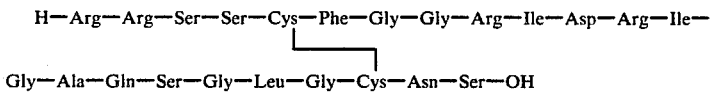

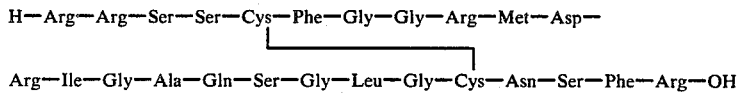

is synthesized using the same general procedure as set forth in Example I. Amino acid analysis shows that the desired peptide structure is obtained. Testing as set forth in Example II shows comparable results.

EXAMPLE XIII

The peptide hANF(8-32), having the formula:

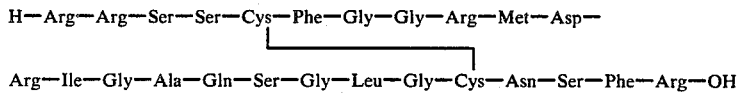

is synthesized using the same general procedure as set forth in Example I. Amino acid analysis shows that the desired peptide structure is obtained. Testing as set forth in Example II shows comparable results.

EXAMPLE XIV

The peptide hANF(8-32)—NH$_2$, having the formula:

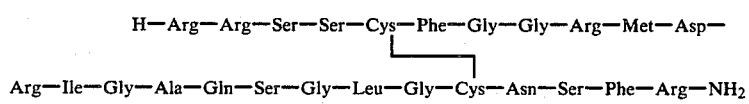

is synthesized as set forth in Example IV. Amino acid analysis shows that the desired peptide structure is obtained. Testing as set forth in Example II shows comparable results.

EXAMPLE XV

The peptide [desArg$^{32}$]-hANF(8-33), having the formula:

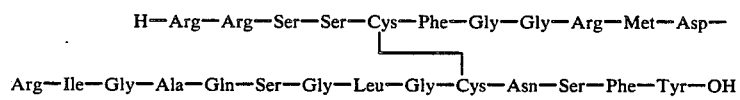

is synthesized using the same general procedure as set forth in Example I. Amino acid analysis shows that the desired peptide structure is obtained. Testing as set forth in Example II shows comparable results.

EXAMPLE XVI

The peptide [desArg$^{32}$]-hANF(5-33), having the formula:

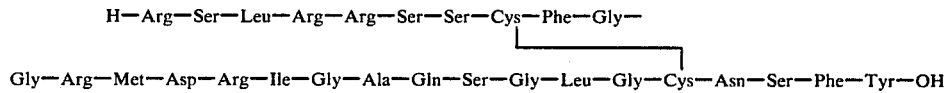

is synthesized using the same general procedure as set forth in Example I. Amino acid analysis shows that the desired peptide structure is obtained. Testing as set forth in Example II shows comparable results.

EXAMPLE XVII

The peptide [desLeu$^7$]-hANF(5-32), having the formula:

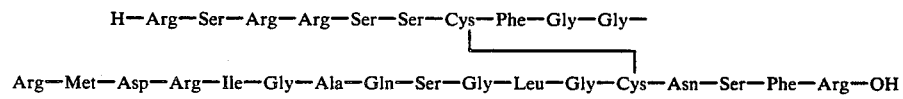

is synthesized using the same general procedure as set forth in Example I. Amino acid analysis shows that the desired peptide structure is obtained. Testing as set forth in Example II shows comparable results.

The observation that synthetic replicates of ANF have the intrinsic activity to modify directly, at the level of the glomerulosa cells, the pattern of aldosterone secretion provides evidence for a humoral link between the heart and the adrenal cortex. While somatostatin, β-endorphin and [Met]-enkephalin have been associated with similar biological activities, the physiological significance is uncertain. The previously known potency of rANF(8-33) and other analogs as natriuretic hormones, coupled with the newly discovered potency to inhibit basal and stimulated aldosterone formation, suggests that the biological activities of ANF are an integral part of the homeostatic mechanisms regulating sodium retention. Furthermore, unlike somatostatin, the inhibitory effect of ANF and its fragments is not restricted to angiotensin-stimulated aldosterone secretion but affects the formation of both basal and stimulated mineralocorticoids. Moreover, at no point was rANF-(8–33) observed to stimulate aldosterone.

These observations provide the groundwork for defining the mechanisms with which atrial-derived peptides affect sodium retention and suggest that ANF may be responsible for the attenuated effects of angiotensin II on the adrenal cortex during sodium loading. It is believed that at least some clinical forms of idiopathic hypo- and hyper-tension may well result from interactions between ANF and the adrenal cortex. The therapeutic implications of these observations are that the administration to humans of specific amounts of ANF peptides can be used to inhibit the secretion of aldosterone, both basal and in response to endogenous ACTH and AN-II, the secretagogues. As a result, it is expected that the administration of ANF peptides for the relief of aldosterone-dependent hypertension may well be an important clinical method of treatment.

The administration of these ANF peptides or the non-toxic addition salts thereof, combined with a pharmaceutically acceptable carrier to form a pharmaceutical composition, may be made to mammals, particularly humans, either intravenously, subcutaneously, intramuscularly, intranasally or orally, and a dosage of between about 1 microgram to about 10 milligrams per kilogram of body weight may be employed to effect management of aldosterone-dependent hypertension under the guidance of a physician who will be able to determine more specific dosages from available test information and the case history of the patient in question.

Such peptides are often administered in the form of pharmaceutically acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, pamoate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

As previously indicated, the peptides should be administered under the guidance of a physician, and pharmaceutical compositions will usually contain the peptide in conjunction with a conventional, pharmaceutically-acceptable carrier. Usually, the dosage will be from about 2 to about 200 micrograms of the peptide per kilogram of the body weight of the host.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, ANF peptides having substitutions and/or modifications in the peptide chain that do not detract from the potency of the analogs may be used.

Various features of the invention are emphasized in the claims which follow.

What is claimed is:

1. A method of decreasing the secretion of aldosterone in a human in need thereof which method comprises administering intravenously, subcutaneously, intramuscularly, intransally or orally to such human an effective amount of a peptide having the formula:

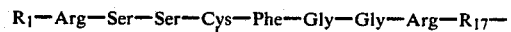
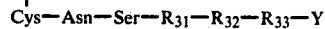

wherein $R_1$ is Arg, Leu-Arg, Ser-Leu-Arg, Arg-Ser-Leu-Arg, Pro-Arg-Ser-Leu-Arg, Gly-Pro-Arg-Ser-Leu-Arg, Ala-Gly-Pro-Arg-Ser-Leu-Arg or Leu-Ala-Gly-Pro-Arg-Ser-Leu-Arg; $R_{17}$ is Met of Ile, $R_{31}$ is Phe or desR$_{31}$; $R_{32}$ is Arg or desR$_{32}$; $R_{33}$ is Tyr or desR$_{33}$; and Y is OH or NH$_2$; or a nontoxic addition salt thereof.

2. A method in accordance with claim 1 wherein $R_{17}$ is Ile.

3. A method in accordance with claim 1 wherein $R_{17}$ is Met.

4. A method in accordance with claim 1 wherein $R_1$ is Arg.

5. A method in accordance with claim 1 wherein $R_{31}$ is Phe.

6. A method in accordance with claim 1 wherein $R_{32}$ is Arg.

7. A method in accordance with claim 1 wherein $R_{33}$ is Tyr.

8. A method in accordance with claim 5 wherein $R_{32}$ is Arg and $R_{33}$ is Tyr.

9. A method in accordance with claim 5 wherein $R_{17}$ is Ile and $R_1$ is Arg.

10. A method in accordance with claim 5 wherein $R_{17}$ is Met and $R_1$ is Arg.

11. A method in accordance with claim 9 wherein $R_{32}$ is Arg.

12. A method in accordance with claim 11 wherein $R_{33}$ is Tyr.

13. A method in accordance with claim 6 wherein $R_{17}$ is Ile.

14. A method in accordance with claim 7 wherein $R_{17}$ is Met.

15. A method in accordance with claim 7 wherein $R_{17}$ is Ile.

16. A method in accordance with claim 1 wherein said peptide has the formula: H-Arg-Arg-Ser-Ser-Cys-Phe-Gly-Gly-Arg-Ile-Asp-Arg-Ile-Gly-Ala-Gln-Ser-Gly-Leu-Gly-Cys-Asn-Ser-Phe-Arg-Tyr-OH.

17. A method in accordance with claim 1 wherein said peptide has the formula: H-Arg-Arg-Ser-Ser-Cys-Phe-Gly-Gly-Arg-Met-Asp-Arg-Ile-Gly-Ala-Gln-Ser-Gly-Leu-Gly-Cys-Asn-Ser-Phe-Arg-Tyr-OH.

18. A method in accordance with claim 1 wherein said peptide is adminstered together with a pharmaceutically acceptable liquid or solid carrier therefor.

* * * * *

UNITED STATES PATENT AND TRADEMARK OFFICE
CERTIFICATE OF CORRECTION

PATENT NO. : 4,643,989

DATED : February 17, 1987

INVENTOR(S) : BAIRD, J. Andrew

It is certified that error appears in the above-identified patent and that said Letters Patent is hereby corrected as shown below:

Column 1, as an initial paragraph, please insert --This invention was made with Government support under Grant No. AM-18811, awarded by the National Institute of Arthritis, Diabetes, and Digestive and Kidney Diseases. The Government has certain rights in this invention.--

Signed and Sealed this

Ninth Day of February, 1993

Attest:

STEPHEN G. KUNIN

Attesting Officer

Acting Commissioner of Patents and Trademarks